United States Patent [19]

Böhm et al.

[11] 4,275,241
[45] Jun. 23, 1981

[54] PROCESS FOR THE PREPARATION OF 3-PHENOXY-BENZALDEHYDES

[75] Inventors: Siegfried Böhm, Cologne; Alfons Klein, Duesseldorf; Karlfried Wedemeyer, Cologne, all of Fed. Rep. of Germany

[73] Assignee: Bayer Aktiengesellschaft, Leverkusen, Fed. Rep. of Germany

[21] Appl. No.: 89,010

[22] Filed: Oct. 29, 1979

[30] Foreign Application Priority Data

Nov. 18, 1978 [DE] Fed. Rep. of Germany ....... 2850180

[51] Int. Cl.$^3$ .................... C07C 45/00; C07C 45/29
[52] U.S. Cl. .................. 568/426; 568/442; 568/637; 568/638
[58] Field of Search .............. 260/600; 568/638, 637, 568/426, 442

[56] References Cited

U.S. PATENT DOCUMENTS

| 3,100,796 | 8/1963 | Trapp et al. | 568/638 |
|---|---|---|---|
| 3,236,898 | 2/1966 | Green et al. | 260/600 |
| 3,322,833 | 5/1967 | McNelis | 260/600 |
| 4,108,904 | 8/1978 | Brown et al. | 260/600 |
| 4,134,925 | 1/1979 | Petersen et al. | 568/638 |

OTHER PUBLICATIONS

Houben–Weyl, Methoden der Organischen Chemie, George Thieme Verby, Struttgart, 1954, 7/1, pp. 171–174.
Wiberg, Oxidation in Org. Chem. Part A, Academic Press, New York, 1965, pp. 145, 146, 151.
Halasz, Soc. Chem. France, Bull. [5] 8, 1941, pp. 170–172, 175–176, 183–185.

Primary Examiner—Howard T. Mars
Attorney, Agent, or Firm—Sprung, Felfe, Horn, Lynch & Kramer

[57] ABSTRACT

A process for the preparation of a-phenoxy-benzaldehyde which comprises contacting the 3-phenoxy-benzyl alcohol of the formula

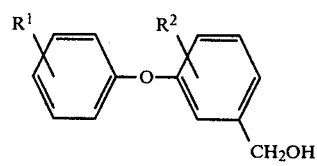

wherein $R^1$ and $R^2$ are identical or different and represent hydrogen or halogen with an aqueous solution of a dichromate in the presence of aqueous sulphuric acid at a temperature in the range of 50° to 125° C. The 3-phenoxy-benzaldehyde can be in a mixture of other organic compounds such as obtained by hydrolyzing a 3-phenoxy toluene chlorinated in the side chain at a temperature of 140°–210° C. under pressure.

11 Claims, No Drawings

PROCESS FOR THE PREPARATION OF 3-PHENOXY-BENZALDEHYDES

The invention relates to a process for the preparation of 3-phenoxy-benzaldehydes from 3-phenoxy-benzyl alcohols or 3-phenoxy-benzyl chlorides.

It is known from DE-OS (German Published Specification) No. 2,741,764 and from DE-OS (German Published Specification) No. 2,704,512 to react a mixture of 3-phenoxy-benzyl chloride and 3-phenoxy-benzal chloride in a first reaction stage with ammonia and formaldehyde or hexamethylenetetramine and then, in a second reaction stage, to hydrolyse the product under acid conditions to 3-phenoxy-benzaldehyde. In the second reaction stage, the reaction product from the first stage is boiled under reflux in a solution containing water, acetic acid and concentrated hydrochloric acid. Corrosion problems arise at this stage when the process is carried out industrially.

A process for the preparation of 3-phenoxy-benzaldehydes from 3-phenoxy-benzyl alcohols has been found which is characterised in that 3-phenoxy-benzyl alcohols of the formula

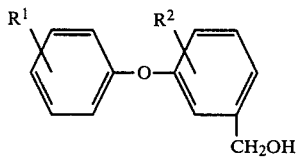

wherein $R^1$ and $R^2$ are identical or different and represent hydrogen or halogen, are oxidized in the presence of aqueous sulphuric acid in the temperature range of 50° to 125° C. with an aqueous solution of a dichromate.

The process according to the invention can be illustrated using the following reaction equation as an example:

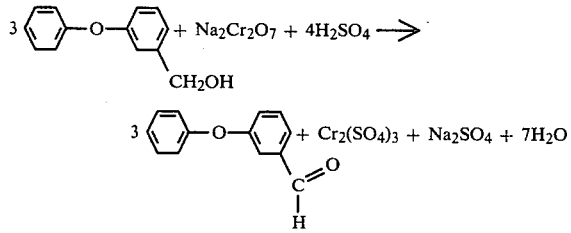

For the process according to the invention, halogen can be fluorine, chlorine, bromine or iodine and preferably fluorine or chlorine.

The 3-phenoxy-benzyl alcohols for the process according to the invention are known and can advantageously be prepared by hydrolysis of 3-phenoxy-benzyl chlorides in the temperature range of 140° to 210° C. under pressure.

The process according to the invention is carried out in the temperature range of 50° to 125° C. and preferably 80° to 100° C. The process according to the invention is generally carried out under normal pressure.

The dichromate used for the process according to the invention is generally an alkali metal dichromate. Examples which may be mentioned are sodium dichromate and potassium dichromate. Of course, it is also possible to use mixtures of different cichromates in the process according to the invention.

In general, 90 to 130 mols and preferably 105 to 120 mols of the dichromate, based on 1 mol of the benzyl alcohol, are employed for the process according to the invention.

For the process according to the invention, the dichromate is generally employed as a 10% by weight to saturated solution and preferably a 20 to 60% by weight aqueous solution.

The sulphuric acid ($H_2SO_4$) content for the process according to the invention can vary within wide limits. It is generally 2.5 to 10 mols and preferably 3 to 7 mols, based on 1 mol of the dichromate.

For the process according to the invention, in general 10 to 70% strength by weight and preferably 20 to 60% strength by weight aqueous sulphuric acid is employed.

The process according to the invention is advantageously carried out in the presence of an inert solvent which is not soluble in water. Such solvents can be, for example, aliphatic or aromatic hydrocarbons, such as, for example, hexane, any iso-octane, benzene or any of the xylenes or mixtures thereof.

In a preferred embodiment of the process according to the invention, a mixture of 3-phenoxy-toluenes, chlorinated in the side chain, of the formula

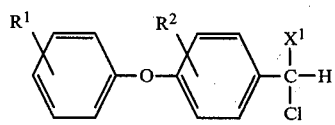

wherein
$X^1$ represents hydrogen or chlorine and
$R^1$ and $R^2$ are identical or different and have the abovementioned meaning,
is hydrolysed in a first reaction stage in the temperature range of 140° to 210° C. under pressure to give a mixture containing 3-phenoxy-benzyl alcohols of the formula (I) and this mixture is then oxidized, in a second reaction stage, in the presence of aqueous sulphuric acid in the temperature range of 50° to 125° C. with an aqueous solution of a dichromate.

3-Phenoxy-toluenes chlorinated in the side chain are in themselves known (DE-OS (German Published Specification) No. 2,704,512). They can be prepared, for example, by chlorination of the corresponding 3-phenoxy-toluenes in carbon tetrachloride in the presence of a free radical initiator or on exposure to light. With a chlorination of this type, 3-phenoxy-benzal chloride, unconverted 3-phenoxy-toluene and in some cases 3-phenoxy-benzotrichloride are also obtained in addition to the 3-phenoxybenzyl chloride.

For the process according to the invention one can use these chlorination mixtures direct, without preliminary separation.

3-Phenoxy-toluenes chlorinated in the side chain which are formed by discontinuing the chlorination of the side chain when a mixture which contains up to 20% by weight of 3-phenoxy-benzal chloride has formed, are preferably employed in the process according to the invention.

The hydrolysis of 3-phenoxy-toluenes chlorinated in the side chain, which are employed according to the preferred embodiment of the process according to the invention, to the mixture containing 3-phenoxy-benzyl alcohols can be carried out in the presence of aqueous bases.

Aqueous bases used for the process according to the invention are, in general, aqueous solutions and/or suspensions of alkali metal or alkaline earth metal oxides, hydroxides or carbonates. The following bases may be mentioned as examples: sodium hydroxide, sodium carbonate, sodium bicarbonate, potassium hydroxide, potassium carbonate, potassium bicarbonate, magnesium oxide, magnesium hydroxide, magnesium carbonate, calcium oxide, calcium hydroxide and calcium carbonate. Preferred bases for the process according to the invention are sodium hydroxide, sodium carbonate, calcium oxide and magnesium oxide.

The alkali metal and alkaline earth metal compounds can be used on their own or as a mixture. It is also possible to start the reaction with one of these compounds and to add another compound during the course of the reaction.

For the process according to the invention, the amount of base can vary within wide limits. In general, the base can be employed in an amount which is 50 to 150 mol % and preferably 75 to 120 mol % of the amount equivalent to the content of side chain chlorine in the 3-phenoxy-benzyl chloride.

For the hydrolysis according to the process of the invention, in general a 0.5 to 10-fold and preferably a 1.5 to 4-fold amount of water, based on the chlorination product employed, is used.

In a preferred embodiment of the process according to the invention the base can be added not at the start of the hydrolysis but only at a later point during the hydrolysis. For example, the base is added after 50 to 85 mol % conversion, based on the content of side chain chlorine in the 3-phenoxy-benzyl chloride. One can also carry out the hydrolysis without the addition of a base.

The hydrolysis can be carried out in several stages. Thus, for example, it is possible to discontinue the reaction after about 40 to 70% of the total conversion, to remove the aqueous phase and to bring the reaction to completion with a new aqueous phase.

The hydrolysis according to the process of the invention is carried out in the temperature range of 140° to 210° C. and preferably of 150° to 190° C. The reaction according to the process of the invention has generally ended after 2 to 7 hours.

The hydrolysis according to the process of the invention can be carried out under excess pressure, in general a pressure in the range of 2 to 100 bars and preferably of 3 to 50 bars. The process according to the invention is appropriately carried out in a pressure vessel, for example an autoclave. The process according to the invention is preferably carried out under the pressure of the reaction mixture which results in the pressure vessel at the reaction temperature chosen.

The process according to the invention can, for example, be carried out as follows:

If appropriate, in a first reaction stage, the 3-phenoxy-toluenes chlorinated in the side chain, water and, optionally, a base are introduced into an autoclave and heated to the reaction temperature. After the reaction has ended, the reaction product can be worked up by methods which are in themselves known. For example, the aqueous layer is separated from the organic phase and a product containing 3-phenoxy-benzyl alcohol is isolated from the organic phase.

In a second reaction stage, this product is oxidised according to the invention to the 3-phenoxy-benzaldehyde.

In order to carry out the oxidation, it is possible to emulsify the 3-phenoxy-benzyl alcohol by stirring with an aqueous solution of chromate and subsequently then to add the sulphuric acid dropwise.

However, it is also possible to mix the 3-phenoxy-benzyl alcohol with the dilute sulphuric acid and then to add the aqueous solution of chromate.

After the reaction has ended, the resulting 3-phenoxy-benzaldehyde can be extracted, for example by extraction, preferably with the inert, non-aqueous solvent optionally added to the reaction. After drying the extraction mixture, the 3-phenoxy-benzaldehyde is obtained by distillation. It is, of course, also possible to isolate the aldehyde via the corresponding bisulphite compound.

It is surprising that 3-phenoxy-benzaldehydes can be prepared by the process according to the invention from 3-phenoxy-benzyl alcohol, with the aid of the oxidation with chromate, which is in itself known, since it is known from Houben-Weyl, Volume 7/1, page 171, (1954) that primary alcohols which also contain ether groups in their molecule are destroyed by chromate.

3-Phenoxy-benzaldehydes of the formula

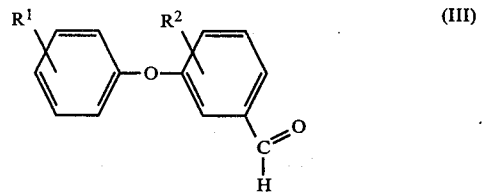

wherein $R^1$ and $R^2$ are identical or different and have the meaning indicated above, can be prepared by the process according to the invention.

The preparation of the 3-phenoxy-benzaldehydes by the process according to the invention takes place with high yields and without by-products which are difficult to work up being obtained. Advantageously, no corrosion problems arise with the reaction.

3-Phenoxy-benzaldehyde is an intermediate product for plant protection agents (Nachrichten aus Chemie, Technik und Laboratorium 26, 120 (1978)).

EXAMPLE 1

A chlorination product of the following composition is hydrolysed:

| | |
|---|---|
| unknown constituents | 1.1% |
| 3-phenoxy-toluene | 46.7% |
| constituents chlorinated in the nucleus | 0.7% |
| 3-phenoxy-benzyl chloride | 46.9% |
| unknown constituents | 1.0% |
| 3-phenoxy-benzal chloride | 3.6% |

The content of side chain chlorine is 10.1%.

150 g of this chlorination mixture, 37.5 g of 50% strength sodium hydroxide solution and 285 g of water are stirred in an autoclave for 3 hours at 180° C. After cooling, the aqueous layer is separated off and the organic phase is distilled over a distillation bridge. At a boiling point $_{1.0}$ up to a temperature of 190° C., 124.6 g of distillate are obtained. A residue of 10.3 g remains.

The distillate has the following composition:

| | |
|---|---|
| unknown constituents | 0.4% |
| 3-phenoxy-toluene | 48.9% |
| constituents chlorinated in the nucleus | 0.6% |
| 3-phenoxy-benzaldehyde | 4.6% |
| unknown constituents | 0.4% |
| 3-phenoxy-benzyl chloride | 0.2% |
| 3-phenoxy-benzyl alcohol | 44.9% |

EXAMPLE 2

150 g of a chlorination product having a composition as in Example 1, 13.3 g of calcium oxide and 300 g of water are stirred for 3 hours in an autoclave at 180° C. After working up, which is carried out analogously to that in Example 1, 124.2 g of distillate are obtained.

A residue of 6.5 g remains.

| Composition of the distillate: | |
|---|---|
| unknown constituents | 0.1% |
| 3-phenoxy-toluene | 51.5% |
| constituents chlorinated in the nucleus | 0.5% |
| 3-phenoxy-benzaldehyde | 3.1% |
| unknown constituents | 0.1% |
| 3-phenoxy-benzyl chloride | 0.1% |
| 3-phenoxy-benzyl alcohol | 44.6% |

EXAMPLE 3

150 g of a chlorination mixture which has the following composition:

| | |
|---|---|
| unknown constituents | 2.3% |
| 3-phenoxy-toluene | 29.8% |
| constituents chlorinated in the nucleus | 1.3% |
| 3-phenoxy-benzyl chloride | 55.1% |
| unknown constituents | 3.0% |
| 3-phenoxy-benzal chloride | 6.5% |

(The content of side chain chlorine is 12.0%) 10.7 g of magnesium oxide and 300 g of water are reacted, and worked up, as described in Example 1.

The resulting distillate weighs 130.5 g. The residue weighs 5.5 g.

| Composition of the distillate: | |
|---|---|
| unknown constituents | 1.2% |
| 3-phenoxy-toluene | 44.1% |
| constituents chlorinated in the nucleus | 1.2% |
| 3-phenoxy-benzaldehyde | 3.0% |
| unknown constituents | 0.6% |
| 3-phenoxy-benzyl chloride | 0.1% |
| 3-phenoxy-benzyl alcohol | 49.7% |

EXAMPLE 4

100 g of a chlorination mixture with the following composition:

| | |
|---|---|
| unknown constituents | 1.6% |
| p-phenoxy-toluene | 19.1% |
| constituents chlorinated in the nucleus | 1.2% |
| 3-phenoxy-benzyl chloride | 64.1% |
| unknown constituents | 1.2% |
| 3-phenoxy-benzal chloride | 12.9% |

(The content of side chain chlorine is 15.9%) 27.3 g of sodium carbonate and 250 g of water are stirred in an autoclave for 3 hours at 180° C. After working up as described in Example 1, 77.1 g of distillate and 6.7 g of residue are obtained.

| Composition of the distillate: | |
|---|---|
| unknown constituents | |
| 3-phenoxy-toluene | 29.7% |
| constituents chlorinated in the nucleus | 1.2% |
| 3-phenoxy-benzaldehyde | 11.3% |
| unknown constituents | 0.6% |
| 3-phenoxy-benzyl chloride | 0.3% |
| 3-phenoxy-benzyl alcohol | 55.9% |

EXAMPLE 5

170 g of a chlorination mixture with the following composition:

| | |
|---|---|
| unknown constituents | 0.7% |
| 3-phenoxy-4-fluoro-toluene | 28.9% |
| constituents chlorinated in the nucleus | 0.3% |
| 3-phenoxy-4-fluoro-benzyl chloride | 63.3% |
| unknown constituents | 0.5% |
| 3-phenoxy-4-fluoro-benzal chloride | 6.3% |

(The content of side chain chlorine is 12.4%) 53 g of 50% strength sodium hydroxide solution and 310 g of water are stirred in an autoclave for 3 hours at 180° C. After cooling, the organic phase is taken up in toluene and separated from the aqueous layer. After distilling off the toluene, 149 g of a reaction product with the following composition:

| | |
|---|---|
| unknown constituents | 0.2% |
| 3-phenoxy-4-fluoro-toluene | 39.3% |
| constituents chlorinated in the nucleus | 0.6% |
| 3-phenoxy-4-fluoro-benzaldehyde | 2.3% |
| unknown constituents | 0.3% |
| 3-phenoxy-4-fluoro-benzyl alcohol | 57.3% |
| remain. | |

EXAMPLE 6

230 g of $H_2O$, 135.2 g of concentrated sulphuric acid and 460 g of toluene are initially introduced into a stirred apparatus. 460 g of a mixture of 3-phenoxy-benzyl alcohol and 3-phenoxy-toluene according to Example 4, which has a 3-phenoxy-benzyl alcohol content, determined by gas chromatography, of 55.9%, are added, with vigorous stirring, and the emulsion is heated to the boil (90° C.) At this temperature, a solution of 135 g of $Na_2O_7 \times H_2O$ in 92 g of $H_2O$ is added dropwise in the course of 40 minutes, the mixture is stirred for a further 30 minutes and cooled and the toluene phase is separated from the chromate liquor. The toluene is distilled off under a waterpump vacuum and the residue is distilled under a high vacuum at 0.5 bar. This gives 430.5 g of a mixture of 3-phenoxy-benzaldehyde and 3-phenoxy-toluene which has a 3-phenoxy-benzaldehyde content, determined by gas chromatography, of 54.6%.

EXAMPLE 7

165 g of $H_2O$ and 132.6 g of $H_2SO_4$ are initially introduced into a stirred apparatus. 165 g of 3-phenoxy-benzyl alcohol are emulsified in the dilute sulphuric acid, by stirring. The emulsion is warmed to 90° C. and at this temperature a solution of 87.8 g of $Na_2Cr_2O_7 \times H_2O$ in 58.5 g of H₂O is added dropwise in the course of 30 minutes. The mixture is stirred for a further 30 minutes and the reaction product is extracted from the chromate liquor using 165 g of toluene. The toluene is evaporated off under a waterpump vacuum and the residue is distilled under a high vacuum. This gives 132.2 g of colorless 3-phenoxy-benzaldehyde which has a purity, determined by gas chromatography, of 98.2%.

EXAMPLE 8

294 g of a mixture of 3-phenoxy-4-fluoro-benzyl alcohol and 3-phenoxy-4-fluoro-toluene according to Example 5, which contains 57.3% of 3-phenoxy-4-fluoro-benzyl alcohol, are emulsified in a mixture of 294 g of water and 128 g of sulphuric acid, with stirring. 294 g of toluene are added and the mixture is heated to the boiling point of the water/toluene azeotrope (90°). At this temperature a solution of 86 g of Na₂Cr₂O₇ × H₂O in 57.0 g H₂O is added dropwise in the course of 30 minutes, the mixture is stirred for a further 30 minutes and cooled and the organic phase is separated from the chromate liquor. This gives 293 g of an organic phase which has a 3-phenoxy-4-fluoro-benzaldehyde content, determined by gas chromatography, of 54.8%.

EXAMPLE 9

960 g of a chlorination product which has the following composition:

| | |
|---|---|
| unknown constituents | 1.5% |
| 3-phenoxy-toluene | 30.3% |
| constituents chlorinated in the nucleus | 0.8% |
| 3-phenoxy-benzyl chloride | 59.1% |
| unknown constituents | 0.8% |
| 3-phenoxy-benzal chloride | 7.5% |

307 g of 50% strength sodium hydroxide solution and 1,758 g of water are stirred in an autoclave for 3 hours at 180° C. After cooling, 852 g of toluene are added, the mixture is rendered slightly acid with sulphuric acid and the aqueous layer is separated off.

In a stirred vessel, this toluene solution is emulsified with 852 g of water and 392 g of concentrated sulphuric acid by stirring well and the emulsion is heated to the boil. The sump temperature is a constant 90° C. A solution of 260 g of sodium dichromate in 173 g of water is added dropwise in the course of 30 minutes and the mixture is stirred for a further 30 minutes. After cooling to 50° C., the aqueous chromate liquor is separated off and the toluene solution is distilled in a 60 cm laboratory packed column.

After the toluene has distilled off, the following fractions are obtained:

| | |
|---|---|
| Fraction 1 boiling point₁₂ 140°–157° C. | 253.6 g |
| Fraction 2 boiling point₁₂ 157°–176° C. | 24.8 g |
| Fraction 3 boiling point₁₂ 176°–178° C. | 378.2 g |
| Residue | 159.6 g |

Fraction 1 consists of 3-phenoxy-toluene and Fraction 3 contains 3-phenoxy-benzaldehyde in a purity of 98.8%.

EXAMPLE 10

150 g of chlorinated material which has the following composition:

| | |
|---|---|
| unknown constituents | 0.9% |
| 3-phenoxy-toluene | 17.9% |
| constituents chlorinated in the nucleus | 2.1% |
| 3-phenoxy-benzyl chloride | 61.3% |
| unknown constituents | 1.3% |
| 3-phenoxy-benzal chloride | 16.8% |
| unknown constituents | 2.0% |

(The content of side chain chlorine is 15.9%) and 480 g of water are stirred in an autoclave for 3 hours at 160° C. The mixture is cooled, the aqueous layer is separated off and, after adding a further 480 g of water, the organic phase is stirred for a further 3 hours at 160° C.

After separating off the aqueous layer, this gives 125 g of an organic phase which has the following composition:

| | |
|---|---|
| unknown constituents: | 0.8% |
| 3-phenoxy-toluene | 21.2% |
| constituents chlorinated in the nucleus | 2.6% |
| 3-phenoxy-benzaldehyde | 12.3% |
| 3-phenoxy-benzyl chloride | 0.9% |
| unknown constituents | 1.8% |
| 3-phenoxy-benzyl alcohol | 60.1% |
| unknown constituents | 0.3% |

Based on the 3-phenoxy-benzyl chloride employed, the yield of 3-phenoxy-benzyl alcohol is 89% of the theoretical conversion.

EXAMPLE 11

120 g of chlorinated material with a composition as in Example 6 and 360 g of water are stirred in an autoclave at 170° C. for a total of 7 hours. A 10% strength sodium hydroxide solution is pumped in in the following amounts: 66 ml after the 1st hour, 35 ml after the 2nd hour, 35 ml after the 4th hour and 30 ml after the 6th hour. After cooling, the aqueous layer is separated off and is distilled as described in Example 2. 98 g of distillate are obtained. A residue of 5 g remains.

The distillate has the following composition:

| | |
|---|---|
| unknown constituents | 0.9% |
| 3-phenoxy-toluene | 19.6% |
| constituents chlorinated in the nucleus | 2.3% |
| 3-phenoxy-benzaldehyde | 14.0% |
| 3-phenoxy-benzyl chloride | 1.1% |
| unknown constituents | 1.3% |
| 3-phenoxy-benzyl alcohol | 60.3% |
| unknown constituents | 0.4% |

Based on the 3-phenoxy-benzyl chloride employed, the yield of 3-phenoxy-benzyl alcohol is 86% of the theoretical conversion.

EXAMPLE 12

150 g of chlorinated material having a composition as in Example 6 and 300 g of water are stirred in an autoclave at 160° C. for a total of 7 hours. 20% strength sodium hydroxide solution is pumped in in the following amounts: 45 ml after the 1st hour, 24 ml after the 2nd hour and 22 ml after the 6th hour. After cooling, the aqueous layer is separated off, a further 300 g of water are added to the organic phase and the latter is stirred for a further 4 hours at 160° C. The organic phase which is separated off is distilled. 121 g of distillate are obtained. A residue of 7.3 g remains.

The distillate has the following composition:

| | |
|---|---|
| unknown constituents | 0.7% |
| 3-phenoxy-toluene | 21.0% |
| constituents chlorinated in the nucleus | 2.8% |
| 3-phenoxy-benzaldehyde | 13.3% |
| 3-phenoxy-benzyl chloride | 0.3% |
| unknown constituents | 1.6% |
| 3-phenoxy-benzyl alcohols | 59.8% |
| unknown constituents | 0.5% |

Based on the 3-phenoxy-benzyl chloride employed, the yield of 3-phenoxy-benzyl alcohol is 86% of the theoretical conversion.

What is claimed is:

1. A process for the preparation of a 3-phenoxy-benzaldehyde which comprises contacting the 3-phenoxy-benzyl alcohol of the formula

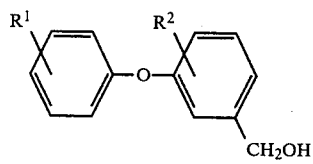

wherein $R^1$ and $R^2$ are identical or different and represent hydrogen or halogen with an aqueous solution of a dichromate in the presence of aqueous sulphuric acid at a temperature in the range of 50° to 125° C.

2. A process according to claim 1 wherein the process is carried out at a temperature in the range of 80° to 100° C.

3. A process according to claim 1 wherein the process is carried out employing 2.5 to 10 mols sulphuric acid to 1 mol of dichromate.

4. A process according to claim 1 wherein the sulphuric acid is employed as a 10 to 70 weight percent aqueous sulphuric acid.

5. A process according to claim 1 wherein the dichromate employed is an alkali metal dichromate.

6. A process according to claim 1 wherein 0.25 to 0.4 mol of dichromate are employed per mol of benzyl alcohol.

7. Process according to claim 1 wherein a 10% by weight to saturated aqueous solution of dichromate is employed.

8. A process according to claim 1 wherein the process is carried out in the presence of an inert solvent which is not soluble in water.

9. A process for the preparation of a 3-phenoxy-benzaldehyde which comprises:

(a) hydrolyzing a 3-phenoxy toluene, chlorinated in the said chain, having the formula

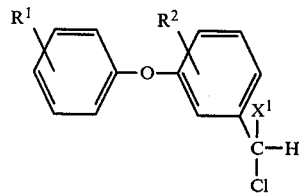

wherein
$X^1$ represents hydrogen or chlorine and
$R^1$ and $R^2$ are identical or different and represent hydrogen or halogen by contacting the same in a first reaction stage with water at a temperature in the range of 140° to 210 ° C. under pressure; and (b) thereafter contacting the resultant product for step (a) with an aqueous solution of a dichromate in the presence of aqueous sulphuric acid at a temperature in the range of 50° 125° C.

10. A process according to claim 9 wherein step (b) is performed without isolation of any 3-phenoxy benzyl alcohol in the reaction product of step (a).

11. A process according to claim 9 wherein the hydrolysis of 3-phenoxy toluene chlorinated in the side chain takes place in a single reaction step.

* * * * *